US011298446B2

(12) United States Patent
Planas et al.

(10) Patent No.: US 11,298,446 B2
(45) Date of Patent: Apr. 12, 2022

(54) SYSTEMS AND METHODS FOR CALIBRATING PUMP STROKE VOLUMES DURING A BLOOD SEPARATION PROCEDURE

(71) Applicant: FENWAL, INC., Lake Zurich, IL (US)

(72) Inventors: Samantha M. Planas, Wauconda, IL (US); Amit J. Patel, Algonquin, IL (US); Kathleen M. Higginson, Mount Prospect, IL (US)

(73) Assignee: Fenwal, Inc., Lake Zurich, IL (US)

( * ) Notice: Subject to any disclaimer, the term of this patent is extended or adjusted under 35 U.S.C. 154(b) by 412 days.

(21) Appl. No.: 14/577,236

(22) Filed: Dec. 19, 2014

(65) Prior Publication Data
US 2016/0175509 A1    Jun. 23, 2016

(51) Int. Cl.
*A61M 1/26*     (2006.01)
*A61M 1/02*     (2006.01)
(Continued)

(52) U.S. Cl.
CPC .......... *A61M 1/267* (2014.02); *A61M 1/0209* (2013.01); *A61M 1/14* (2013.01); *A61M 1/265* (2014.02); *A61M 1/3496* (2013.01); *A61M 60/50* (2021.01); *A61M 60/113* (2021.01); *A61M 60/268* (2021.01); *A61M 60/279* (2021.01); *A61M 2205/3334* (2013.01); *A61M 2205/702* (2013.01)

(58) Field of Classification Search
CPC .................................................... A61M 1/267
See application file for complete search history.

(56) References Cited

U.S. PATENT DOCUMENTS

| 5,112,298 A | * | 5/1992 | Prince .................... A61M 1/30 210/645 |
| 5,733,257 A | | 3/1998 | Sternby |

(Continued)

FOREIGN PATENT DOCUMENTS

| CN | 103561798 A | 2/2014 |
| EP | 0723463 B1 | 3/2001 |

(Continued)

OTHER PUBLICATIONS

European Search Report, counterpart EP Appl. No. 15200418 dated May 12, 2016.

(Continued)

*Primary Examiner* — Peter Keyworth
(74) *Attorney, Agent, or Firm* — Cook Alex Ltd.

(57) ABSTRACT

A method is provided for calibrating a pump during a blood separation procedure that has at least a first and second state or phase where fluid is flowed to or from a reservoir by action of the pump. The state or phase of the procedure may be a priming state, a draw state, a separation state and a return state, and the pump calibration may be performed between consecutive performances of the same procedure state. The calibration is based on a variance between the volume of fluid predicted to be processed by the pump for the given state of the procedure and the actual volume processed based on the change of weight of the reservoir. Recalibration of the pump, if necessary, is accomplished before the performance of the second phase is commenced.

22 Claims, 6 Drawing Sheets

(51) Int. Cl.
*A61M 1/14* (2006.01)
*A61M 1/34* (2006.01)
*A61M 60/50* (2021.01)
A61M 60/113 (2021.01)
A61M 60/268 (2021.01)
A61M 60/279 (2021.01)

(56) References Cited

U.S. PATENT DOCUMENTS

| | | | |
|---|---|---|---|
| 5,932,103 A | 8/1999 | Kenley et al. | |
| 6,042,532 A * | 3/2000 | Freed | A61M 1/1062 600/18 |
| 6,280,634 B1 | 8/2001 | Shah et al. | |
| 6,691,047 B1 | 2/2004 | Fredericks | |
| 6,890,157 B2 | 5/2005 | Pfeil et al. | |
| 6,984,218 B2 | 1/2006 | Nayak et al. | |
| 7,338,802 B2 | 3/2008 | Frischauf et al. | |
| 7,421,316 B2 | 9/2008 | Gray et al. | |
| 7,556,611 B2 | 7/2009 | Kolenbrander et al. | |
| 7,993,297 B2 | 8/2011 | Vinci et al. | |
| 8,075,468 B2 | 12/2011 | Min et al. | |
| 8,235,931 B2 | 8/2012 | Burbank et al. | |
| 8,753,515 B2 | 6/2014 | Curtis et al. | |
| 8,852,140 B2 | 10/2014 | Barry, Jr. et al. | |
| 2002/0033370 A1 * | 3/2002 | Bainbridge | A61M 1/3693 210/782 |
| 2010/0113891 A1 * | 5/2010 | Barrett | A61B 5/14535 600/301 |
| 2012/0132574 A1 | 5/2012 | Ware et al. | |
| 2012/0310135 A1 | 12/2012 | Bauer et al. | |
| 2013/0008854 A1 | 1/2013 | Wallace et al. | |
| 2013/0338559 A1 | 12/2013 | Franano et al. | |
| 2014/0291243 A1 | 10/2014 | Curtis et al. | |

FOREIGN PATENT DOCUMENTS

| | | |
|---|---|---|
| EP | 0846470 B1 | 9/2003 |
| EP | 1458431 B1 | 1/2009 |
| EP | 1357958 B1 | 8/2010 |
| EP | 2289577 A1 | 3/2011 |
| EP | 2476447 A1 | 7/2012 |
| EP | 2442847 B1 | 8/2013 |
| EP | 1129291 B1 | 12/2014 |
| WO | WO9300120 A1 | 1/1993 |
| WO | WO 95/10310 | 4/1995 |
| WO | WO 01/18396 A1 | 3/2001 |
| WO | WO 03/011376 A2 | 2/2003 |
| WO | WO 03/055542 A1 | 7/2003 |
| WO | WO 2004/066121 A2 | 8/2004 |
| WO | WO 2005/039671 A2 | 5/2005 |
| WO | WO 2007/133259 A1 | 11/2007 |
| WO | WO 2010/025826 A2 | 3/2010 |
| WO | WO 2010/146342 A2 | 12/2010 |
| WO | WO 2011/068885 A1 | 6/2011 |
| WO | WO 2012/163516 A1 | 12/2012 |

OTHER PUBLICATIONS

China National Intellectual Property Administration, Search Report for counterpart application No. 201510864011.9, dated Mar. 25, 2019 (2 pages).

* cited by examiner

SYSTEMS AND METHODS FOR CALIBRATING PUMP STROKE VOLUMES DURING A BLOOD SEPARATION PROCEDURE

BACKGROUND

Field of the Disclosure

The invention relates to fluid separation systems and methods. More particularly, the invention relates to systems employing spinning membranes for fluid separation and methods for operating such systems.

Description of Related Art

Various blood processing systems now make it possible to collect particular blood constituents, instead of whole blood, from a blood source such as, but not limited to, a container of previously collected blood or other living or non-living source. Typically, in such systems, whole blood is drawn from a blood source, a particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents (e.g., red cells, platelets, and plasma) through centrifugation, such as in the AMICUS® separator from Fenwal, Inc. of Lake Zurich, Ill., or other centrifugal separation devices, or a spinning membrane-type separator, such as the AUTOPHERESIS-C® and AURORA® devices from Fenwal, Inc. Such separation devices typically comprise a fluid circuit having a separation chamber, sources or containers of various solutions, and collection containers that are interconnected by tubing and which is mounted onto a durable hardware component that includes pumps, clamps, and sensors that are automatically operated by a programmable controller to perform the desired blood separation procedure.

Operation of the system to perform the desired procedure requires control of the fluid flow rates and volumes of fluid circulated through the various components of the fluid circuit. Fluid flow through the fluid circuit is caused by operation of the pumps acting on the tubing segments associated therewith. Flow rates through the tubings caused by the pumps may vary from procedure to procedure, and even during the course of a single procedure, due to factors such as variations in the tubing comprising the fluid circuit, changes in inlet pressure, variations in how the fluid circuit is mounted to the durable hardware component, variations in the characteristics of the biological fluid being processed (such as variations in hematocrit), etc. Given the potential for variation in flow rates and volumes, it is necessary to monitor and, if necessary, adjust the operation of the pumps to insure that the separation procedure is safely and efficiently performed. By way of the present disclosure, systems and methods for calibrating pump stroke volumes during a blood separation procedure are provided.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In a first aspect, a method is provided for calibrating a pump during a blood separation procedure that has at least a first and second state or phase where fluid is flowed to or from a reservoir by action of the pump. The state or phase of the procedure may be one or more of a priming state, a draw state, a separation state and a return state, and the pump calibration may be performed between consecutive performances of the same procedure state.

The method includes the steps of: providing a predetermined value for the flow rate of fluid to or from the reservoir for the first state of the procedure; obtaining the weight of the reservoir at the beginning of the first state of the procedure; operating the pump to perform the first state of the procedure; obtaining the weight of the reservoir at the end of the first state of the procedure; comparing the weight of the reservoir at the beginning of the first state of the procedure to the weight of the reservoir at the end of the first state of the procedure to determine an actual flow rate of fluid to or from the reservoir; determining the variance between the actual flow rate and the predetermined value for the flow rate; and adjusting the value for the predetermined flow rate for the second state of the procedure based on the variance. Preferably, the weight is converted to a volume by knowledge of the density of the fluid being pumped, and then determining the flow rate as a volume per unit time.

In another aspect of the method, the value for the predetermined flow rate for the pump is obtained based on a nominal pump cycle or stroke volume for the pump and an anticipated number of pump cycles or strokes to be performed by the pump during the performance of the first state.

In a further aspect, the predetermined value for the flow rate for the second state of the procedure is adjusted if a calculated pump volume for the first state of the procedure exceeds a predetermined amount. In one example, the predetermined value for the flow rate for the second state of the procedure is adjusted if the calculated pump volume for the first state of the procedure is from 10 mL to 1000 mL, and more preferably from 50 mL to 600 mL.

In another aspect of the method, a limit is set for the amount by which the predetermined flow rate will be adjusted for the second state of the procedure if the variance between the predetermined value for the flow rate and the actual flow rate is greater than or equal to ($\geq$) a set percentage or volume, in which case the predetermined value for the flow rate for the second state of the procedure is adjusted by no more than the set percentage or volume. The set percentage may be within a range, e.g., of from 1% to 50%, and preferably of from 5% to 25%. Similarly, the set volume may be in a range of from 1 mL/min to 50 mL/min, and preferably from 5 mL/min to 25 mL/min.

In a further aspect of the method, the pump may be a blood pump and the state of the procedure may be a separation state or a return state; the pump may be an anticoagulant or AC pump and the state of the procedure may be a prime state or a draw state; or the pump may be a concentrated cell pump and the state of the procedure may be a separation state.

In a related aspect, a blood processing system for processing whole blood or a whole blood component is provided in which the processing system comprises at least one pump and a controller with a user interface and has a fluid flow circuit with at least one reservoir associated therewith, and the controller is configured to perform the methods of any one, or combination of, the aspects described above.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
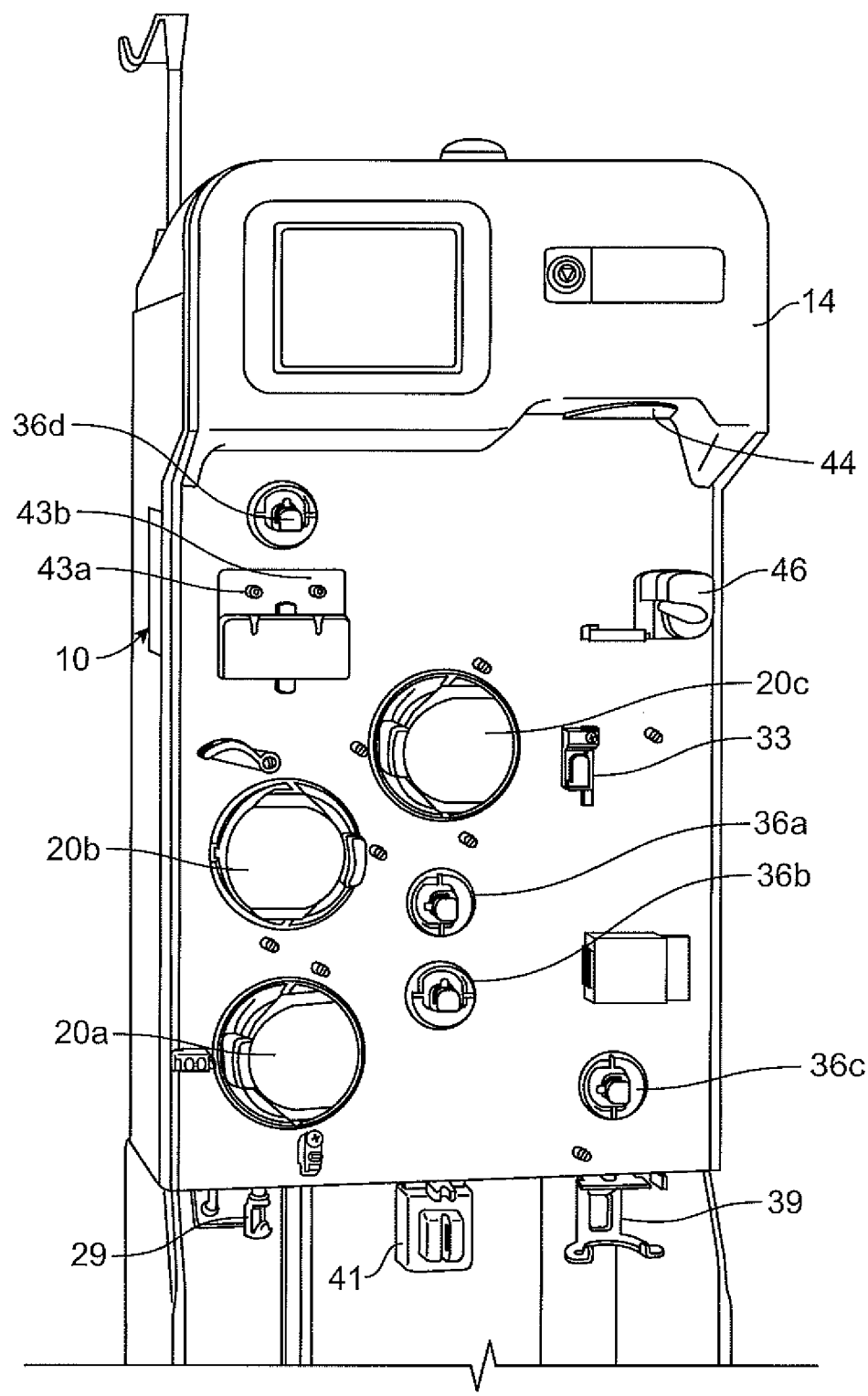
FIG. 1 is a front perspective view of an exemplary fluid separation system suitable for performing the method of the present disclosure.
Figure 2:
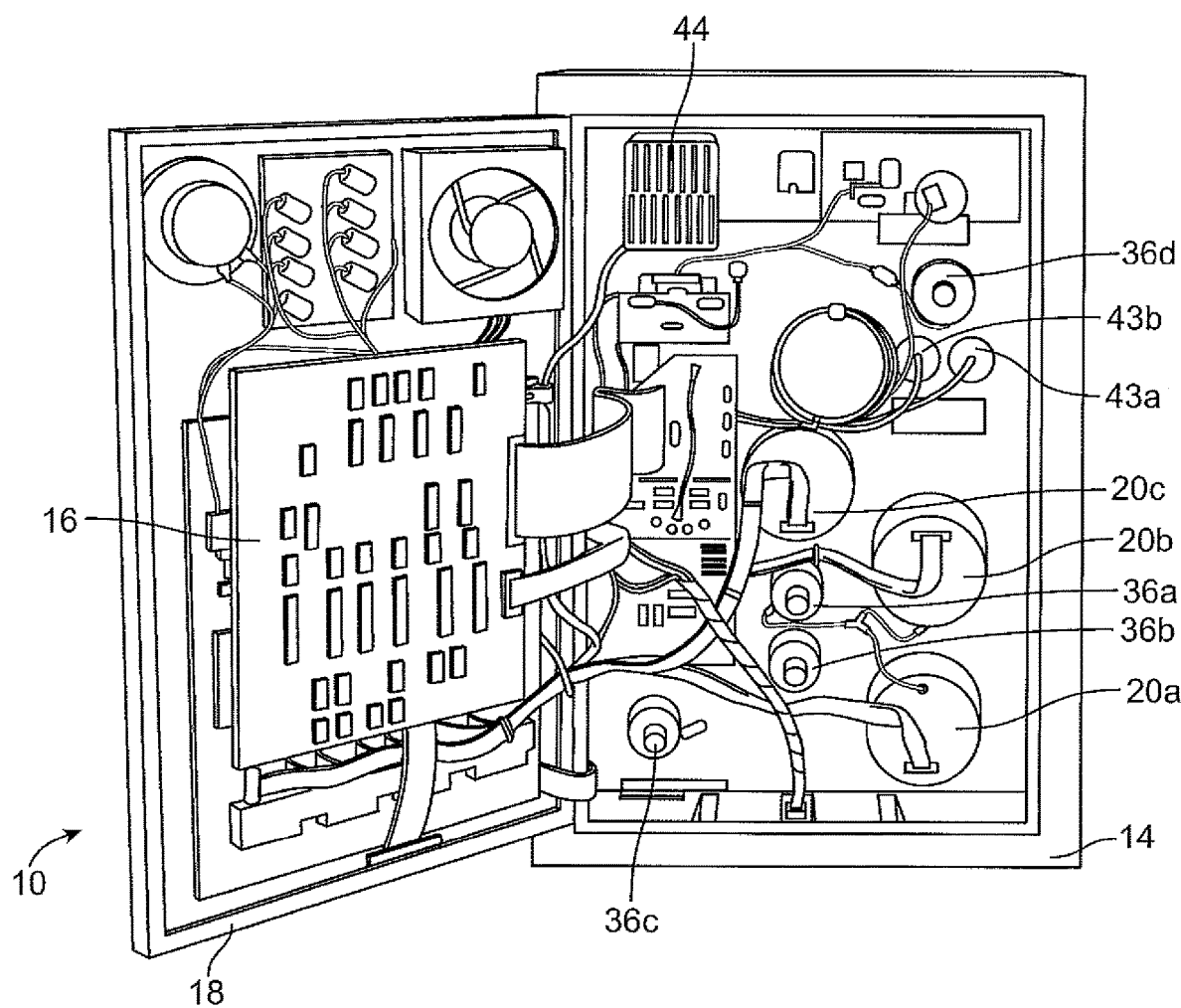
FIG. 2 is a rear perspective view of the fluid separation system of FIG. 1, with a rear door thereof in an open position.
Figure 3:
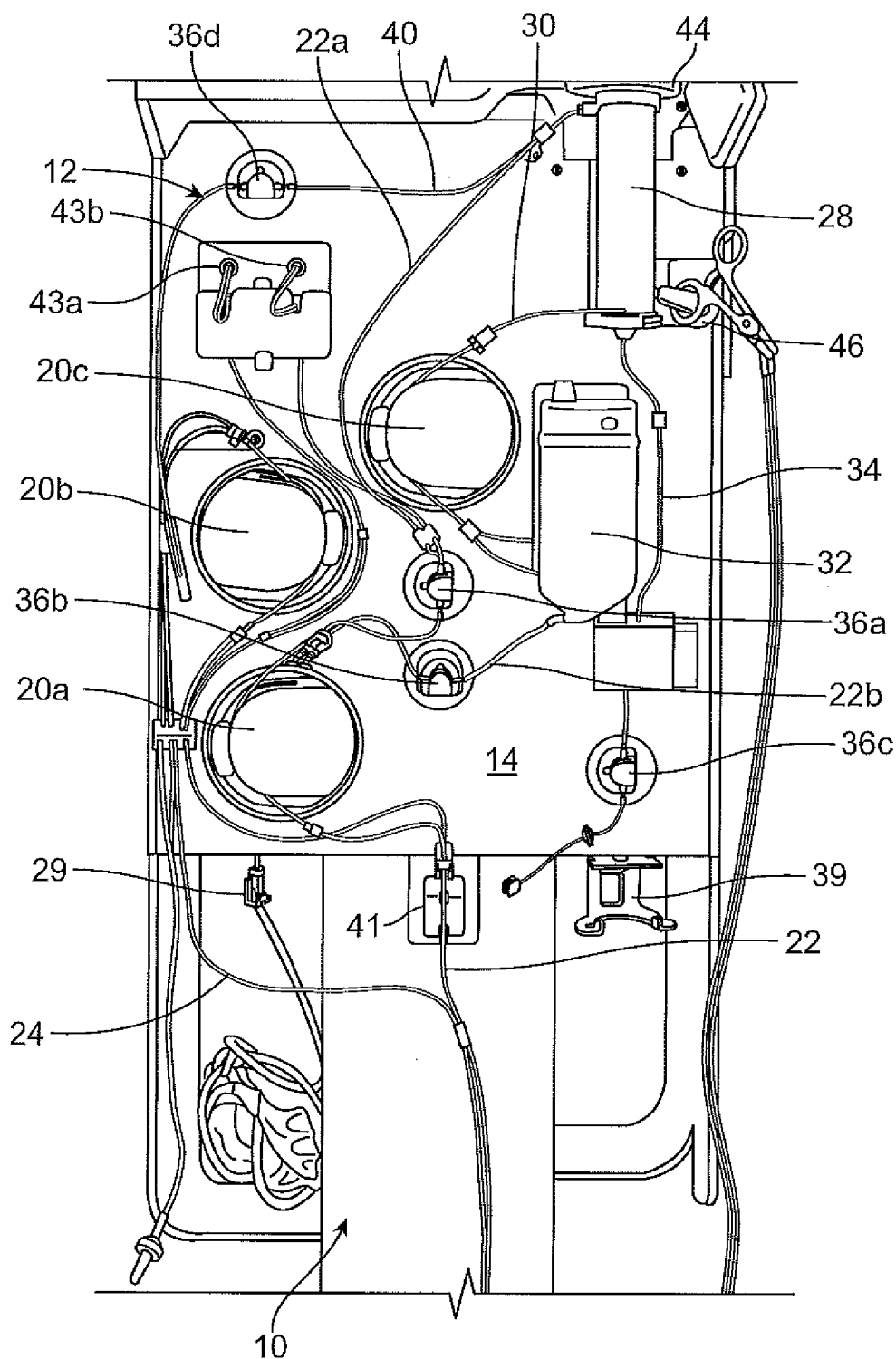
FIG. 3 is a front perspective view of the fluid separation system of FIG. 1, with a fluid flow circuit associated therewith.

According to an aspect of the present disclosure, a durable or reusable fluid separation system is used in combination with a separate fluid flow circuit (which may be disposable) to separate a fluid into two or more constituent parts. FIGS. 1 and 2 illustrate an exemplary fluid separation system 10, while FIG. 3 illustrates an exemplary fluid flow circuit 12 mounted onto the fluid separation system 10, but it should be understood that the illustrated fluid separation system 10 and fluid flow circuit 12 are merely exemplary of such systems and circuits and that differently configured fluid separation systems and fluid flow circuits may be provided without departing from the scope of the present disclosure.

Figure 5:
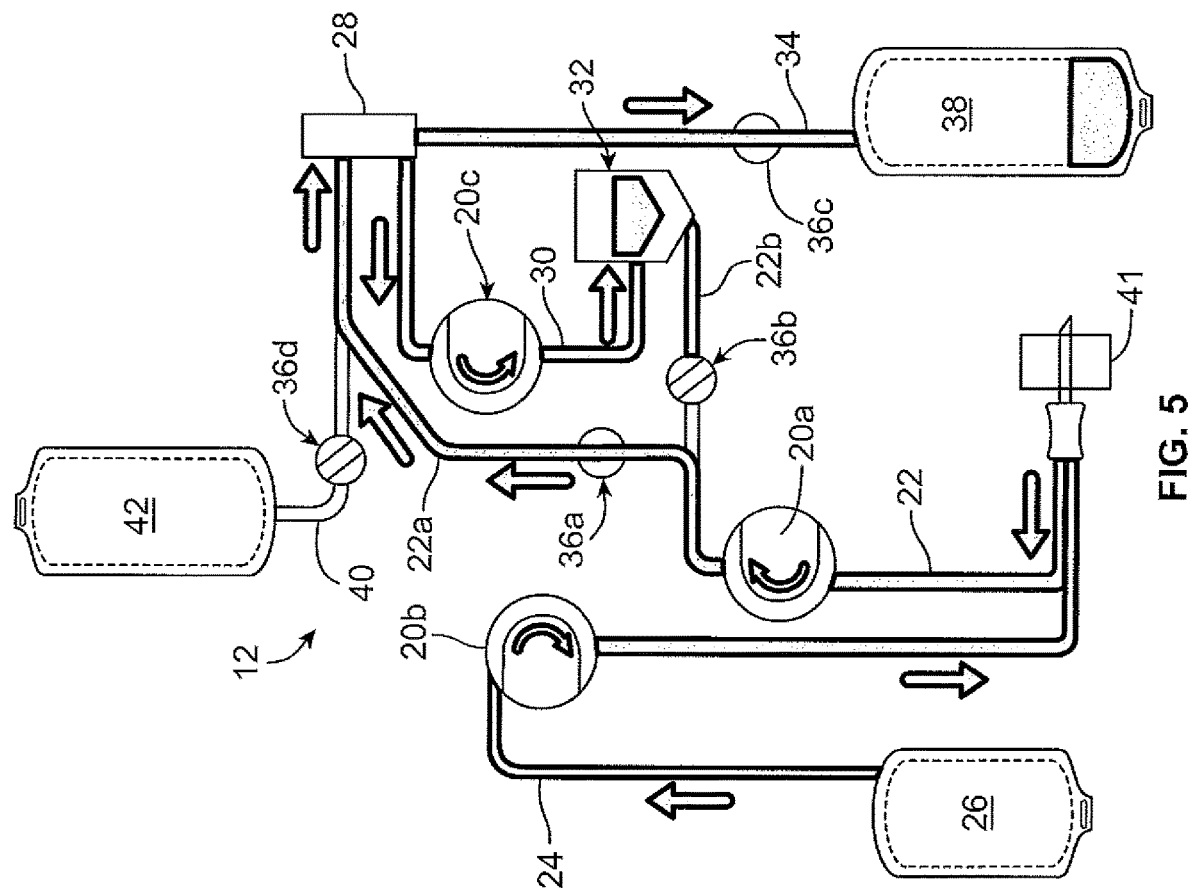
FIG. 5 is a schematic view of the fluid flow circuit and fluid separation system of FIG. 3, in a fluid draw mode.

The system 10 of FIG. 1 is configured for processing whole blood, but it may be used to process other biological fluids. The fluid may come from any fluid source during a draw or collection phase of the procedure (see, e.g., FIG. 5) and be returned to any recipient, which may be the same as or different from the fluid source, during a return or reinfusion stage (see, e.g., FIG. 6). In one embodiment, the fluid source/recipient is a living donor or patient (e.g., a human blood donor), while in other embodiments the fluid source and/or fluid recipient may be a non-living source/recipient (e.g., a blood bag or fluid container).

The illustrated system 10 includes a cabinet or housing 14, with several components positioned outside of the cabinet 14 (e.g., associated with a front wall or surface or panel of the cabinet 14) and additional components (including a programmable central processing unit or controller 16) and interconnects positioned inside of the cabinet 14, which may be accessed by opening a rear door 18 of the system 10, as shown in FIG. 2. Among the system components positioned on the outside of the cabinet 14, one or more pumps or pump stations 20a-20c may be provided, with the pumps 20a-20c configured to accommodate tubing lines of the fluid flow circuit 12.

One of the pumps 20a may be provided as a source/recipient access pump, which may be associated with a source/recipient access line 22 of the fluid flow circuit 12 and operates to draw fluid from a fluid source (FIG. 5) during the draw or collection phase, operates in reverse to return fluid to a fluid recipient (FIG. 6) during the reinfusion stage, and is stopped at the end of the reinfusion phase. Pump 20a also primes the fluid flow circuit 12 and clears air from the access line 22. Pump 20a may also be referred to herein as a "blood pump," as it serves to pump whole blood from its source (such as a donor or, in the case of previously collected blood, a container or reservoir) to the separation module or chamber 28, described below. Pump 20a is also used to return the non-targeted blood components.

Another one of the pumps 20b may be provided as an anticoagulant pump, which may be associated with an anticoagulant line 24 of the fluid flow circuit 12 and operates to add anticoagulant from an anticoagulant source or container 26 of the fluid flow circuit 12 (FIG. 5) to fluid drawn from the fluid source in the source/recipient access line 22 before the fluid enters into a fluid separation module or chamber 28 of the fluid flow circuit 12. The anticoagulant container 26 is supported by a weigh scale hanger 29. Pump 20b does not, however, operate during the reinfusion phase of the procedure. Pump 20b may also be referred to herein as an "AC pump."

A third pump 20c may be provided as a return fluid pump, which may be associated with a return fluid outlet line 30 and operates to draw a return fluid (i.e., a fluid constituent to be returned to a fluid recipient) from the fluid separation chamber 28 and direct it into a return fluid reservoir 32 after the fluid has been separated into a return fluid and a collection fluid in the fluid separation chamber 28. The return fluid reservoir is supported by the weigh scale hanger 33. The pump 20c may also be used to prime the fluid flow circuit 12 and assist in clearing fluid from the fluid separation module 28 at the end of the procedure. Pump 20c does not, however, operate during the reinfusion phase of the procedure. Pump 20c may also be referred to herein as a "cell pump," as it serves to deliver cellular concentrate (i.e., concentrated red blood cells) to the return fluid reservoir 32 in a plasmapheresis procedure.

In the illustrated embodiment, the pumps 20a-20c are peristaltic pumps, but it is within the scope of the present disclosure for differently configured pumps, such as diaphragm or other pumps, to be provided. Furthermore, additional or alternative pumps may be provided without departing from the scope of the present disclosure. For example, a pump may be associated with a collection fluid outlet line 34 of the fluid flow circuit 12 to draw a collection fluid from the fluid separation chamber 28 after the fluid from the fluid source has been separated into a return fluid and a collection fluid. Also, as will be described in greater detail herein, the illustrated embodiment employs a single fluid flow tubing or flow path for both drawing fluid from a source and flowing or returning it to a recipient, which are carried out intermittently. The system 10 could employ separate draw and return flow paths or tubes without departing from the scope of the present disclosure.

In addition to the pumps 20a-20c, the external components of the system 10 may include one or more clamps or valves 36a-36d associated with the tubing lines of the fluid flow circuit 12. The clamps or valves 36a-36d may be variously configured and operate to selectively allow and prevent fluid flow through the associated tubing line. In the illustrated embodiment, one clamp or valve 36a may be provided as a fluid source/recipient clamp, which may be associated with a draw branch 22a of the source/recipient access line 22 of the fluid flow circuit 12 to allow (FIG. 5) or prevent (FIG. 6) the flow of fluid through the draw branch 22a of the source/recipient access line 22. Another one of the clamps or valves 36b may be provided as a reinfusion clamp or valve, which may be associated with a reinfusion branch 22b of the source/recipient access line 22 downstream of a return fluid reservoir 32 of the fluid flow circuit 12 to allow (FIG. 6) or prevent (FIG. 5) the flow of return fluid through the reinfusion branch 22b. A third clamp or valve 36c may be provided as a collection fluid clamp or valve, which may be associated with the collection fluid outlet line 34 to allow (FIG. 5) or prevent (FIG. 6) the flow of collection fluid through the collection fluid outlet line 34 and into a collection fluid container 38, which is supported by the weigh scale hanger 39. A fourth clamp or valve 36d may be provided as a replacement fluid clamp or valve, which may be associated with a replacement fluid line 40 of the fluid flow circuit 12 to allow or prevent the flow of a replacement fluid out of a replacement fluid source 42 (e.g., a bag or container at least partially filled with saline). Additional or alternative clamps or valves may also be provided without departing from the scope of the present disclosure.

The illustrated system 10 further includes one or more pressure sensors 43a and 43b that may be associated with the fluid flow circuit 12 to monitor the pressure within one or more of the tubing lines of the fluid flow circuit 12 during operation of the pumps 20a-20c and clamps or valves 36a-36d. In one embodiment, one pressure sensor 43a may be associated with a tubing line that draws fluid from a fluid source and/or directs processed fluid to a fluid recipient, while the other pressure sensor 43b may be associated with a tubing line that directs fluid into or out of the fluid separation chamber 28 to assess the pressure within the fluid separation chamber 28, but the pressure sensors 43a and 43b may also be associated with other tubing lines without departing from the scope of the present disclosure. The pressure sensors 43a and 43b may send signals to the system controller 16 that are indicative of the pressure within the tubing line or lines being monitored by the pressure sensor 43a, 43b. If the controller 16 determines that an improper pressure is present within the fluid flow circuit 12 (e.g., a high pressure due to an occlusion of one of the tubing lines), then the controller 16 may instruct one or more of the pumps 20a-20c and/or one or more of the clamps or valves 36a-36d to act so as to alleviate the improper pressure condition (e.g., by reversing the direction of operation of one of the pumps 20a-20c and/or opening or closing one of the clamps or valves 36a-36d). Additional or alternative pressure sensors may also be provided without departing from the scope of the present disclosure. In addition, the system 10 preferably includes an air detector 41 associated with the donor line 22 to provide a signal to the controller 16 when air is detected in the donor line.

Figure 4:
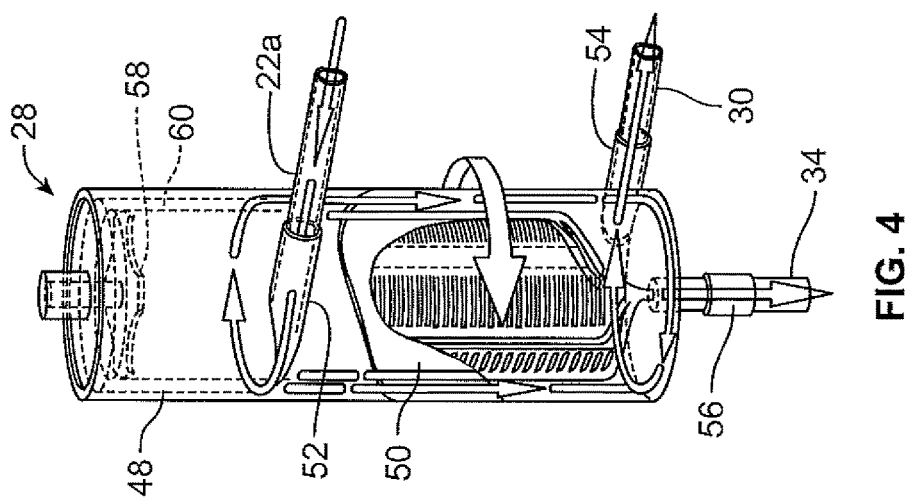
FIG. 4 is a front perspective view of a fluid separation chamber of the fluid flow circuit of FIG. 3, with a portion thereof broken away for illustrative purposes.

The system 10 may also include a separation actuator 44 that interacts with a portion of the fluid separation chamber 28 to operate the fluid separation chamber 28. A chamber lock 46 may also be provided to hold the fluid separation chamber 28 in place with respect to the system cabinet 14 and in engagement with the separation actuator 44. The configuration and operation of the separation actuator 44 depends upon the configuration of the fluid separation chamber 28. In the illustrated embodiment, the fluid separation chamber 28 is provided as a spinning membrane-type separator, such as a separator of the type described in greater detail in U.S. Pat. Nos. 5,194,145 and 5,234,608 or in PCT Patent Application Publication No. WO 2012/125457 A1, each of which is incorporated herein by reference. If provided as a spinning membrane-type separator, the fluid separation chamber 28 may include a tubular housing 48 (FIG. 4), with a microporous membrane 50 positioned therein. An inlet 52 allows a fluid from a fluid source to enter into the housing 48 (via the draw branch 22a of the source/recipient access line 22), while a side outlet 54 allows return fluid to exit the housing 48 (via the return fluid outlet line 30) and a bottom outlet 56 allows collection fluid to exit the housing 48 (via the collection fluid outlet line 34) after the fluid from the fluid source has been separated into return fluid and collection fluid.

In the illustrated embodiment, the separation actuator 44 is provided as a driver that is magnetically coupled to a rotor 58 on which the membrane 50 is mounted, with the separation actuator 44 causing the rotor 58 and membrane 50 to rotate about the central axis of the housing 48. The rotating rotor 58 and membrane 50 create Taylor vortices within a gap 60 between the housing 48 and the membrane 50, which tend to transport the return fluid away from the membrane 50 to exit the fluid separation chamber 28 via the side outlet 54, while the collection fluid passes through the membrane 50 toward the central axis of the housing 48 to exit the fluid separation chamber 28 via the bottom outlet 56. In one embodiment, whole blood from a blood source is separated into cellular blood components (return fluid) and substantially cell-free plasma (collection fluid). It should be understood that the present disclosure is not limited to a particular fluid separation chamber and that the illustrated and described fluid separation chamber 28 is merely exemplary. For example, in other embodiments, a differently configured spinning membrane-type fluid separation chamber may be employed (e.g., one in which the membrane 50 is mounted on an inside surface of the housing 48 or on both the rotor 58 and an inside surface of the housing 48 and facing the gap 60) without departing from the scope of the present disclosure.

The membrane 50 of the fluid separation chamber 28 may be variously configured without departing from the scope of the present disclosure. When the system 10 is to be used to separate blood into two or more constituents, at least a portion of the membrane 50 preferably has anti-thrombogenic characteristics to prevent or at least decrease the incidence of reaction, such as protein or platelet activation upon the blood being separated within the fluid separation chamber 28. As used herein, the term "anti-thrombogenic" is intended to refer to a substance or property characterized by an enhanced resistance to the accumulation of blood components than the materials typically employed in the manufacture of membranes of spinning membrane-type fluid separation chambers (e.g., nylon 6-6).

Any suitable membrane material (or combination of materials) and anti-thrombogenic material (or combination of materials) may be used in manufacturing the membrane 50. In one embodiment, the membrane 50 is formed of a polymeric material (e.g., nylon 6-6, polyethersulfone, polysulfone, polycarbonate, polyvinylidene fluoride, polyamide, or the like), with an anti-thrombogenic material (e.g., polyethylene glycol or any one of the additives or coatings provided by Interface Biologics, Inc. of Toronto, Canada, or the like) incorporated or mixed or blended therein. In another embodiment, the membrane 50 is fully formed from a polymeric material (e.g., nylon, polyethersuflone, polysulfone, polycarbonate, polyvinylidene fluoride, polyamide, or the like) and then an anti-thrombogenic material (e.g., polyethylene glycol, any one of the additives or coatings provided by Interface Biologics, Inc. of Toronto, Canada, or the like) is applied to or coated onto at least a portion of the formed membrane 50.

Figure 6:
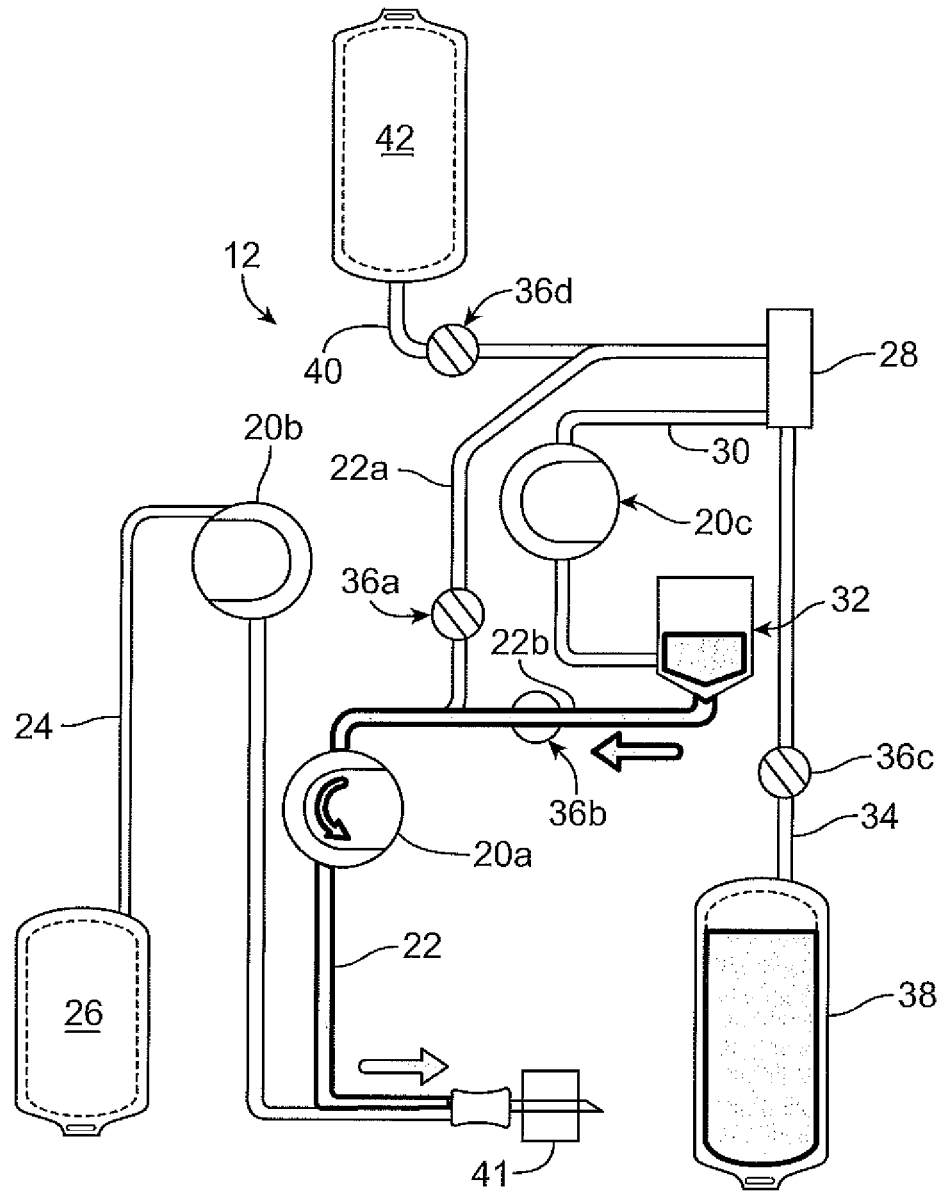
FIG. 6 is a schematic view of the fluid flow circuit and fluid separation system of FIG. 3, in a fluid return mode.

According to one method of using the fluid separation system 10 and fluid flow circuit 12, a fluid is drawn from a fluid source into the fluid separation chamber 28 during a draw or collection phase or mode (FIG. 5), where the fluid is separated into return fluid (e.g., concentrated cellular blood components) and collection fluid (e.g., substantially cell-free plasma). The collection fluid is retained by the system 10, while the return fluid is stored in the reservoir 32 and then returned to the fluid source during a return or reinfusion phase or mode (FIG. 6). In one embodiment, the sequential performance of the draw and return phases (drawing from the fluid source, separating the fluid from the fluid source into return fluid and collection fluid, pumping the collection fluid to the fluid source or a different recipient, and returning the return fluid to the fluid source) are repeated until a target (e.g., a particular amount of collection fluid) is achieved. All of the draw phases and all of the return phases may be identical or may differ from each other. For example, a final draw phase may draw less fluid from the fluid source than the previous draw phases and a final return phase may infuse a combination of return fluid and replacement fluid to the fluid recipient, whereas the previous return phases pump only return fluid to the fluid recipient.

In accordance with the disclosure, a method is provided for calibrating a pump during a blood separation procedure that has at least a first and second state or phase where fluid is flowed to or from a reservoir by action of the pump. The state or phase of the procedure may be a priming state, a draw state, a separation state and a return state, and the pump calibration may be performed between consecutive performances of the same procedure state. In the context of the system 10 described above, the reservoir may be any one or more of the AC container 26, return fluid reservoir 32, collection container 38, and replacement fluid source 42, depending on the phase of the procedure being performed. For example, if the separation phase of the procedure is being performed, the "reservoir" would include both the return fluid reservoir 32 and the collection container 38, as both have fluid flowed thereto during the separation phase by pumps 20*a* and 20*c*. Thus, the pump may be any one or more of pumps 20*a*, 20*b* and 20*c*.

Figure 7:
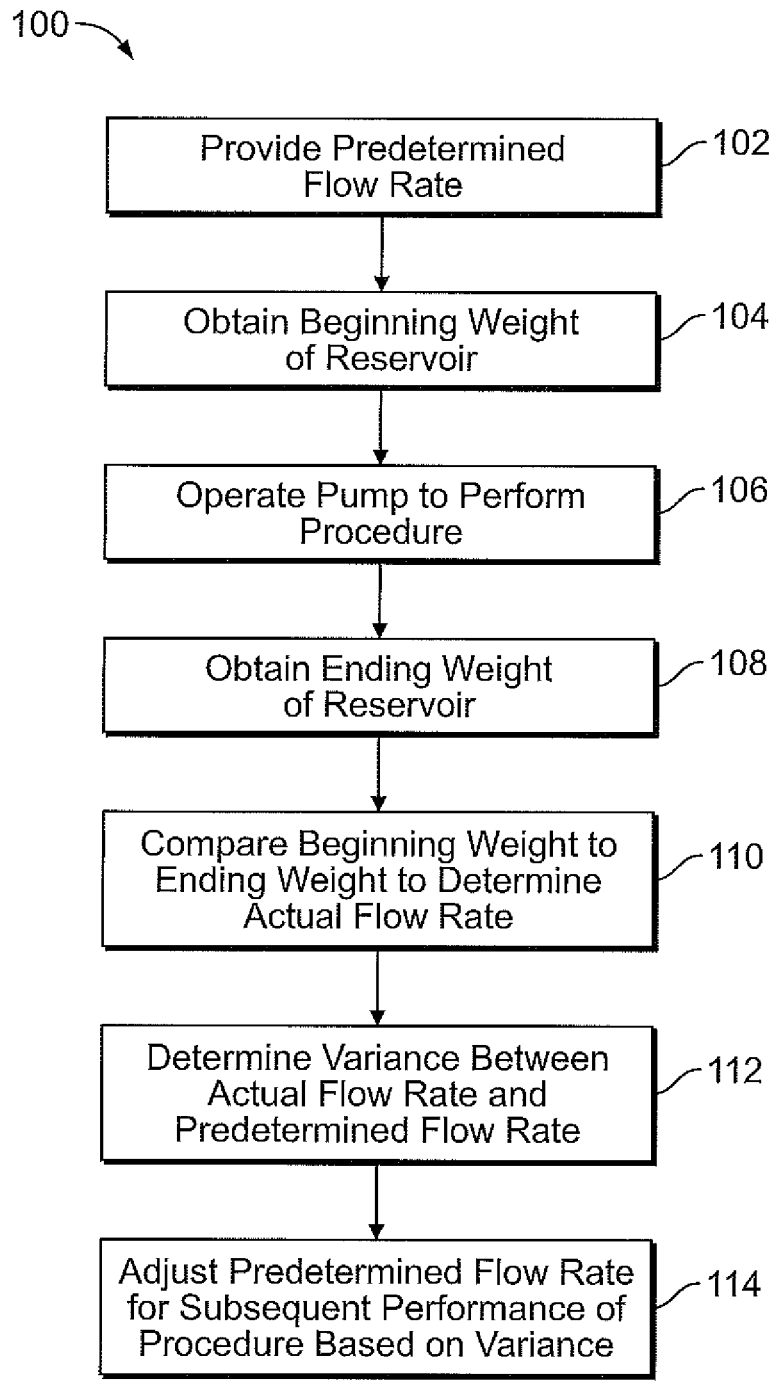
FIG. 7 is a flow chart schematically illustrating the various steps of the pump calibration method of the present disclosure.

Turning to FIG. 7, the steps of the pump calibration method, generally designated 100, are schematically illustrated. As contemplated, the steps of the method are preferably automatically implemented by the system controller 16, described above. The method 100 has an initial step 102 of providing a predetermined flow rate of fluid to or from the reservoir or "pump efficiency" for the first state of the procedure. This predetermined flow rate may be input to the controller by an operator or preprogrammed into the controller. The initial predetermined flow rate is typically determined empirically. For example, the initial predetermined flow rate for the pump may obtained based on a nominal pump cycle or stroke volume for the pump and an anticipated number of pump cycles or strokes to be performed by the pump during the performance of the first state of the procedure.

The weight of the reservoir at the beginning of the first state of the procedure is obtained, as indicated by step 104. The weight of the reservoir may be obtained, e.g., by a weigh scale that supports or is otherwise associated with the reservoir, such as weigh scales 29 and 33 described above, and which transmits a signal indicative of the weight to the system controller 16.

The pump is then operated to perform the first state of the procedure, as indicated by step 106. At the end of the first state of the procedure, the weight of the reservoir obtained and transmitted to the system controller, as indicated by step 108, and the weight of the reservoir at the beginning of the first state procedure is compared by the system controller to the weight of the reservoir at the end of the first state of the procedure to determine an actual flow rate of fluid to or from the reservoir, as indicated by step 110.

The system controller then determines the variance between the actual flow rate and the predetermined flow rate, as indicated by step 112, and the predetermined flow rate or "pump efficiency" to be used when performing the second state of the procedure is adjusted by the system controller based on the variance, as indicated by step 114. It may be that the pump is used for a different state or phase of the separation procedure before it is re-used for performing the second state of the procedure. Thus weight measurements, flow rates, and pump efficiencies may be stored by the system controller for a period of time before the recalibration is actually performed.

In order to ensure that pump recalibration has a meaningful basis, the amount of fluid pumped during the phase should be sufficiently great so that permissible tolerances in, e.g., measurement of the reservoir weight, and noise inherent in the system do not dominate the determination of the variance between the calculated and measured flow rates. Thus, in keeping with a further aspect of the method, the predetermined flow rate for the second state of the procedure is adjusted if the calculated pump volume for the first state of the procedure exceeds a predetermined amount. In one non-limiting example, the predetermined flow rate for the second state of the procedure is adjusted if the calculated pump volume for the first state of the procedure is from 10 mL to 1000 mL, and more preferably from 50 mL to 600 mL.

Similarly, it may also be desirable to limit the magnitude of the maximum permissible pump recalibration adjustment from the first state to the second state. For example, even if the variance between the predetermined flow rate and the actual flow rate is greater than or equal to ($\geq$) a predetermined percentage, the predetermined flow rate for the second state of the procedure is adjusted by no more than the predetermined percentage. The predetermined percentage may be in a range of, e.g., from 1% to 50%, and preferably from 5% to 25%. In a non-limiting example, the predetermined percentage may be 10%, in which case if the variance between the predetermined flow rate and the actual flow rate exceeds 10%, the predetermined flow rate for the second state of the procedure will be adjusted by no more than 10%. Alternatively, the maximum permissible pump recalibration adjustment may be a specified flow rate, within a range of, e.g., from 1 mL/min to 50 mL/min, and preferably form 5 mL/min to 25 mL/min. In a non-limiting example, predetermined flow rate may be 10 mL/min, in which case if the variance between the predetermined flow rate and the actual flow rate exceeds 10 mL/min, the predetermined flow rate for the second state of the procedure will be adjusted by no more than 10 mL/min.

There may be instances where it would be appropriate for the system to automatically adjust, or prompt the system operator to adjust, other parameters for the separation procedure in response to automatic recalibration of the pumps. For example, if automatic recalibration would result in a slower cell pump speed or an increased blood pump speed during the draw state, it may be desirable to adjust the separation parameters by, e.g., reducing the target hematocrit of the return fluid to reduce the likelihood of hemolysis. Alternatively, the controller could by default always reduce the target hematocrit of the return fluid at the beginning of each draw cycle.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

Without limiting any of the foregoing, the subject matter herein may be found in one or more methods or apparatus. For example, in a first aspect, a method is provided for calibrating a pump during a blood separation procedure that has at least a first and second state or phase where fluid is flowed to or from a reservoir by action of the pump. The state or phase of the procedure may be a priming state, a draw state, a separation state and a return state, and the pump calibration may be performed between consecutive performances of the same procedure state. The method includes the steps of: providing a predetermined value for the flow rate of fluid to or from the reservoir for the first state of the procedure; obtaining the weight of the reservoir at the beginning of the first state of the procedure; operating the pump to perform the first state of the procedure; obtaining the weight of the reservoir at the end of the first state of the procedure; comparing the weight of the reservoir at the beginning of the first state procedure to the weight of the reservoir at the end of the first state of the procedure to determine an actual flow rate of fluid to or from the reservoir; determining the variance between the actual flow rate and the predetermined value for the flow rate; and adjusting the value for the predetermined flow rate for the second state of the procedure based on the variance.

In another aspect of the method, the value for the predetermined flow rate for the pump is obtained based on a nominal pump cycle or stroke volume for the pump and an anticipated number of pump cycles or strokes to be performed by the pump during the performance of the first state.

In a further aspect, the predetermined value for the flow rate for the second state of the procedure is adjusted if a calculated pump volume for the first state of the procedure exceeds a predetermined amount. In one example, the predetermined value for the flow rate for the second state of the procedure is adjusted if the calculated pump volume for the first state of the procedure is the calculated pump volume for the first state of the procedure is from 10 mL to 1000 mL, and more preferably from 50 mL to 600 mL.

In another aspect of the method, a maximum permissible pump recalibration adjustment from the first state to the second state is limited to a predetermined amount that is less than the variance between the predetermined flow rate and the actual flow rate, the predetermined amount being from 1% to 50%, and preferably from 5% to 25%. Alternatively, a maximum permissible pump recalibration adjustment from the first state to the second state is limited to a predetermined amount that is less than the variance between the predetermined flow rate and the actual flow rate, the predetermined amount being from 1 mL/min to 50 mL/min, and preferably from 5 mL/min to 25 mL/min.

In a further aspect of the method, the pump may be a blood pump and the state of the procedure may be a draw state or a return state; the pump may be an anticoagulant or AC pump and the state of the procedure may be a prime state or a draw state; or the pump may be a return or cell pump and the state of the procedure may be a separation state.

In a related aspect, a blood processing system for processing whole blood or a whole blood component is provided in which the processing system comprises at least one pump and a controller with a user interface and has a fluid flow circuit with at least one reservoir associated therewith, and the controller is configured to perform the methods of any one, or combination of, the aspects described above.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description, but is set forth in the following claims.

The invention claimed is:

1. A method for adjusting a pump flow rate during a blood separation procedure having an initial performance of a first state and a second performance of the first state where fluid is flowed to or from a reservoir by the pump, the pump flow rate being adjusted between the initial and second performances of the first state, the method comprising:
   a) establishing a minimum volume of fluid to be pumped during the initial performance of the first state of the procedure in an amount to account for permissible tolerances;
   b) providing a predetermined value for a flow rate of fluid to or from the reservoir for the initial performance of the first state of the procedure;
   c) weighing the reservoir at the beginning of the initial performance of the first state of the procedure;
   d) operating the pump to flow fluid to or from the reservoir to perform the initial performance of the first state of the procedure;
   e) weighing the reservoir at the end of the initial performance of the first state of the procedure;
      comparing the weight of the reservoir at the beginning of the initial performance of the first state of the procedure to the weight of the reservoir at the end of the initial performance of the first state of the procedure to determine an actual volume of fluid pumped during the initial performance of the first state of the procedure and to determine an actual flow rate of fluid to or from the reservoir;
   g) comparing the minimum volume of fluid to be pumped during the initial performance of the first state of the procedure to the actual volume of fluid pumped during the first state of the procedure;
   h) if the actual volume of fluid pumped during the initial performance of the first state of the procedure exceeds the minimum volume of fluid to be pumped, then determining a variance between the actual flow rate and the predetermined value for the flow rate;
   i) calculating a pump volume for the initial performance of the first state of the procedure;
   j) adjusting the predetermined value for the flow rate for the second performance of the first state of the procedure based on the variance, wherein a maximum permissible adjustment of the predetermined value for the flow rate from the initial performance of the first state to the second performance of the first state is limited to a predetermined amount that is less than the variance between the predetermined value for the flow rate and the actual flow rate; and k) operating the pump at the predetermined value for the flow rate for the second performance of the first state of the procedure to flow fluid to or from the reservoir to perform the second performance of the first state of the procedure.

2. The method of claim 1 wherein the predetermined value for the flow rate for the initial performance of the first state of the procedure is obtained based on a nominal pump stroke volume and an anticipated number of pump strokes to be performed by the pump.

3. The method of claim 1 wherein the first predetermined amount is the calculated pump volume for the first state of the procedure is from 10 mL to 1000 mL.

4. The method of claim 1 wherein the second predetermined amount is from 1% to 50%.

5. The method of claim 1 wherein the second predetermined amount is from 1 mL/min to 50 mL/min.

6. The method of claim 1 wherein the pump is a blood pump and the first state of the procedure is a draw state.

7. The method of claim 1 wherein the pump is a blood pump and the first state of the procedure is a return state.

8. The method of claim 1 wherein the pump is a cell pump and the first state is a separation state.

9. The method of claim 1 wherein the pump is an AC pump and the first state of the procedure is a prime state.

10. The method of claim 1 wherein the pump is an AC pump and the first state of the procedure is a draw state.

11. The method of claim 1 in which the pump is a cell pump and the fluid in the reservoir is a return fluid that has a target hematocrit, the method further comprising reducing the target hematocrit of the fluid in the reservoir if the pump recalibration adjustment results in a slower pump speed.

12. The method of claim 1 in which the pump is a blood pump and the fluid in the reservoir is a return fluid that has a target hematocrit, the method further comprising reducing the target hematocrit of the fluid in the reservoir if the pump recalibration adjustment results in an increased pump speed.

13. In a blood separation procedure comprising one or more of a priming state, a draw state, a separation state and a return state and utilizing a system comprising a fluid circuit with at least one reservoir and a pump for flowing fluid through the fluid circuit during each state, a method for adjusting a pump flow rate for consecutive performances of the same procedure state, comprising:

a) establishing a minimum volume of fluid to be pumped during the initial performance of a selected first state of the procedure in an amount to account for permissible tolerances;

b) providing a predetermined value for a flow rate of fluid to or from the reservoir for the selected first state of the procedure;

c) weighing the reservoir at the beginning of the initial performance of the selected first state of the procedure;

d) operating the pump to flow fluid to or from the reservoir for the initial performance of the selected first state of the procedure;

e) weighing the reservoir at the end of the initial performance of the selected first state of the procedure;

f) comparing the weight of the reservoir at the beginning of the initial performance of the selected first state of the procedure to the weight of the reservoir at the end of the initial performance of the selected first state of the procedure to determine an actual volume of fluid pumped during the initial performance of the selected first state of the procedure and to determine an actual flow rate of fluid to or from the reservoir;

g) comparing the minimum volume of fluid to be pumped during the initial performance of the selected first state of the procedure to the actual volume of fluid pumped during the initial performance of the selected first state of the procedure;

h) if the actual volume of fluid pumped during the initial performance of the selected first state of the procedure exceeds the minimum volume of fluid to be pumped, then determining a variance between the actual flow rate and the predetermined value for the flow rate;

i) calculating a pump volume for the initial performance of the selected first state of the procedure;

j) adjusting the predetermined value for the flow rate for a subsequent performance of the selected first state of the procedure based on the variance wherein a maximum permissible adjustment of the predetermined value for the flow rate from the initial performance of the selected first state to the subsequent performance of the selected first state is limited to a predetermined amount that is less than the variance between the predetermined value for the flow rate and the actual flow rate; and k) operating the pump at the predetermined value for the flow rate for the subsequent performance of the selected first state of the procedure to flow fluid to or from the reservoir for the subsequent performance of the same state of the procedure.

14. The method of claim 13 wherein the predetermined value for the flow rate for the initial performance of the selected first state of the procedure is obtained based on a nominal pump stroke volume and an anticipated number of pump strokes to be performed by the pump.

15. The method of claim 13 wherein the predetermined amount is from 10 mL to 1000 mL.

16. The method of claim 13 wherein the second predetermined amount is from 1% to 50%.

17. The method of claim 13 wherein the second predetermined amount is from 1 mL/min to 50 mL/min.

18. The method of claim 13 wherein the pump is a blood pump and the selected first state of the procedure is a draw state.

19. The method of claim 13 wherein the pump is a blood pump and the selected first state of the procedure is a return state.

20. The method of claim 13 wherein the pump is a cell pump and the selected first state of the procedure is a separation state.

21. The method of claim 13 in which the pump is a cell pump and the fluid in the reservoir is a return fluid that has a target hematocrit, the method further comprising reducing the target hematocrit of the fluid in the reservoir if the pump recalibration adjustment results in a slower pump speed.

22. The method of claim 13 in which the pump is a blood pump and the fluid in the reservoir is a return fluid that has a target hematocrit, the method further comprising reducing the target hematocrit of the fluid in the reservoir if the pump recalibration adjustment results in an increased pump speed.

* * * * *